(12) United States Patent
Majari Kasmaee (10) Patent No.: US 10,777,835 B2
(45) Date of Patent: Sep. 15, 2020

(54) BIOLOGICAL-ALKALI ION HYBRID BATTERY

(71) Applicant: Laleh Majari Kasmaee, Pacific Palisades, CA (US)

(72) Inventor: Laleh Majari Kasmaee, Pacific Palisades, CA (US)

( * ) Notice: Subject to any disclaimer, the term of this patent is extended or adjusted under 35 U.S.C. 154(b) by 205 days.

(21) Appl. No.: 16/006,152

(22) Filed: Jun. 12, 2018

(65) Prior Publication Data

US 2019/0181483 A1 Jun. 13, 2019

Related U.S. Application Data

(60) Provisional application No. 62/520,314, filed on Jun. 15, 2017.

(51) Int. Cl.
| | | |
|---|---|---|
| *H01M 8/16* | (2006.01) | |
| *H01M 8/1009* | (2016.01) | |
| *H01M 2/02* | (2006.01) | |
| *C12N 9/02* | (2006.01) | |
| *H01M 4/90* | (2006.01) | |

(52) U.S. Cl.
CPC ............ *H01M 8/16* (2013.01); *C12N 9/0004* (2013.01); *H01M 2/0247* (2013.01); *H01M 4/90* (2013.01); *H01M 8/1009* (2013.01)

(58) Field of Classification Search
CPC ........ H01M 8/16; H01M 8/1009; H01M 4/90; H01M 2/02
See application file for complete search history.

(56) References Cited

U.S. PATENT DOCUMENTS

| | | | | |
|---|---|---|---|---|
| 2010/0310945 | A1* | 12/2010 | Premier ................. | H01M 8/16 429/401 |
| 2012/0321966 | A1* | 12/2012 | Wallin ................... | H01M 8/16 429/401 |
| 2013/0084474 | A1* | 4/2013 | Mills ................... | H01M 4/9016 429/9 |

OTHER PUBLICATIONS

Monzon et al., "Microbial fuel cells under extreme salinity: performance and microbial analysis", Abstract, Jun. 20, 2014.*

* cited by examiner

*Primary Examiner* — Kenneth J Douyette
(74) *Attorney, Agent, or Firm* — BioPatent; Gary Baker (57) ABSTRACT

Microbial fuel cells (MFCs) that employ bioactive materials at the anode and alkaline metal ions at the cathode. The bioactive materials can include microbes and/or enzymes to convert an organic feed stock into electron donors to be received at the anode. The MFCs can beneficially be housed in an anaerobic environment.

25 Claims, 5 Drawing Sheets

BIOLOGICAL-ALKALI ION HYBRID BATTERY

FIELD OF THE INVENTION

The present invention relates to a microbial or biological fuel cell which can directly convert reducing equivalents generated from oxidization of an organic fuel by, e.g., a halotolerant or halophile organism into electric current. The cell cathode typically consuming the reducing equivalents through alkali ion intercalation and reduction.

BACKGROUND OF THE INVENTION

Microbial fuel cells can theoretically be useful in various applications, such as in wastewater treatment, and/or in renewable energy production, but serious issues of efficiency and reliability still have existed. While a microbial fuel cell according to the present invention may be used in place of conventional microbial fuel cells (MFCs), it can be uniquely designed to advantageously generate power in air-less and oxygen-less environments, such as outer space. Despite ongoing research in the area of microbial fuel cells, their previous output power density and efficiency of fuel conversion to energy performance has limited MFCs' production and application. There remains a continuous demand for improvement in the field of microbial and bio fuel cells.

Microbial fuel cells may be used as a method of wastewater treatment coupled to electricity generation, or as a method of renewable energy generation from non-waste products. Some bio-electrochemical systems may be used as a method of fuel (hydrogen or methane) generation. Microbial fuel cells can, in theory, use any microbial digest or metabolic product for fuel to generate electricity. Wastewater, biomass, or any other substrate of choice, can be provided as a biodegradable fuel oxidized by microorganisms in microbial fuel cells directly. Alternatively, the wastewater is biodegradable to produce other products that can be oxidized by microorganism in a microbial fuel cell.

In their most conventional form, MFCs utilize microorganisms to catalyze the oxidation reaction at the anode. The diversity of microorganisms that can be used as the catalyst at an anode widens the fuel choices in comparison with the current preprocessed fuel choices for fuel cells. This is due to existence of specific reaction pathways in the presence of microorganisms, which can reduce the anodic overpotential of fuel oxidation.

Microbial and biological fuel cells offer the potential to employ an organism or a part of the organism (such as enzymes or protein extracts from the organisms) to convert energy stored in organic carbon compounds (waste) into electricity. A biological fuel cell refers to an energy generation device wherein at least one of the two electrochemical reactions (i.e., oxidation at anode (negative electrode) and reduction at cathode (positive electrode)), is catalyzed using an organism or a part of the organism. Biofuel cells that employ microorganism are more specifically classified as MFC. The catalytic activity of MFC is generated, e.g., by microbes (generally, bacteria) that attach to the conductive surfaces of electrodes (anodes and/or cathode) and form electrochemically active biofilms.

In cases that MFCs contain anodophilic microorganisms in anodic compartment, microbes within a biofilm at the anode can enzymatically extract electrons from organic components in an aqueous solution and transfer the electrons to the electrode, while producing protons. The protons generated typically pass through a cation-permeable membrane (e.g., a Nafion membrane) towards cathode. The electrons flow from the anode through the electrical connection between the anode and cathode, producing a current. At the cathode, the electrons can combine protons and oxygen (typically, final electron-acceptor or oxidant) to form water. In the embodiments of MFCs with cathodophilic microorganisms, microbes within the biofilm at the cathode enzymatically transfer electrons from the cathode to an oxidant. The power produced by such a fuel cell can be used as a power supply.

Since MFC systems are designed to immediately move the electrical energy away from the anode to the cathode through electrical current generation, the microbes are unable to use the energy for growing and for building biomass. Furthermore, the movement of energy away from the microbes also accelerates microbial metabolism and increases primary waste reduction rates.

The electrocatalytic function of microorganisms for fuel oxidation can be understood by studying the metabolism of the fuel in living organisms. We find fuels can include, but are not limited to, sugars (for example, glucose, fructose, lactose, etc.), organic acids and metabolic intermediates (for example, lactate, acetate, etc.), biopolymers (for example, cellulose, chitosan, etc.), and mixed waste streams (for example, compost, wastewater, food wastes, etc.).

For a fuel such as acetate, the metabolism mechanism can be divided into two separate chemical half-reactions. The first half-reaction is the oxidation of acetate to produce carbon dioxide, protons, and electrons at the anode:

$$CH_3COO^- + 4H_2O \rightarrow 2HCO_3^{2-} + 9H^+ + 8e^-$$

and the second half-reaction is the reduction of an electron acceptor such as oxygen to form water at the cathode:

$$2O_2 + 8H^+ + 8e^- \rightarrow 4H_2O$$

When the oxidation half-reaction and reduction half-reaction are combined, the overall reaction for metabolism of acetate is:

$$CH_3COO^- + 2O_2 \rightarrow 2HCO_3^{2-} + H^+$$

The energy released in this reaction is used in living organisms to generate ATP, which serves as an energy carrier in cells to drive biochemical reactions. The energy is harnessed by coupling the generation of protons and electrons to enzymes that generate ATP. If these electrons and protons are diverted from ATP generation in the cell, they can be used to power a fuel cell. In theory, the oxygen reduction coupled with oxidation of acetate creates a maximum voltage of 1.1 V. However open circuit potentials of a well-controlled laboratory MFC usually do not exceed 0.8 V. While MFCs can be used to convert organic contaminants in wastewater into electric energy, the low voltage has been a problem limiting practical applications in large scale wastewater treatment plants.

To form a biocatalyst on the anode, the anodophilic bacteria can be incubated by placing the anode in the organic material oxidizable by the bacteria under oxidizing reaction conditions including maintenance of substantially anaerobic conditions. In the case of anodophilic microbes that transfer electrons through a mediator, the microbes are not required to be present on the anode surface, but may exist elsewhere in the anodic chamber, and still produce electrons that are successfully transferred to anode through the mediator.

There are a variety of technical problems with MFCs known in prior art. The traditional choice of oxidant for fuel cells, and microbial fuel cells is oxygen. This choice is mostly rationalized based on the fact that oxygen is naturally available in the air. However, the kinetics of oxygen reduction reaction is slow, and the overpotential of this reaction is about 400 mV. Even to achieve such potentials, expensive catalysts of platinum metal group are required. In old art MFCs with air or oxygen cathodes, a membrane as a barrier to oxygen entry into the anode chamber is placed between the anodic and cathodic chambers. Most commonly, a cation or proton exchange membrane, such as a perfluorinated sulfonic acid polymer or NAFION, which is substantially impermeable to oxygen is used in MFCs for this purpose. Although it is well known that oxygen reduction reaction is sluggish and rate determining step in the MFC, the least amount of attention has been focused on new solutions for the cathode problem.

Oxygen solubility in water is quite low and greatly hinders half-cell reactions dependent on oxygen. Oxygen solubility in water is influenced by water temperature, atmospheric pressure, and salinity. At 25° C. in the presence of 1 atmosphere of air, oxygen concentration in freshwater is about 6 mg/L, and this value decreases at higher temperatures and higher salinity levels. Due to low solubility of oxygen in water, direct air cathodes were developed. While direct air cathodes improve the amount of oxidant availability at the cathode, water leakage can become an expensive obstacle. The outer surface of a cathode can be covered by a cathode diffusion layer (CDL), which is preferably bonded to the cathode, to prevent water leakage through the cathode from the interior of the reaction chamber. However, the CDL needs to be oxygen permeable, allowing gaseous oxygen or air to freely diffuse from the outside of reaction chamber into the catalyst in the cathode. Further, it may be necessary to include a hydrogen permeable hydrophobic polymer material, such as polytetrafluoroethylene (PTFB), to the CDL. To minimize the water leakage, the thickness of this material is varied or multiple layers are required. These measures can greatly inhibit the efficiency of the cell in operation.

Where fuel oxidation by the microorganisms is done in anaerobic conditions, using the oxygen as the oxidant dictates complete separation of anodic and cathodic compartments, otherwise the parasite reactions such as aerobic oxidation of fuel, which does not generate free electrons to be transferred the anode to produce an electric current, will drastically reduce the cell voltage and current output. The requirement for a barrier, (e.g., an ion-exchange membrane), between the anode and the cathode causes structural restrictions for the MFC system design. The presence of membrane brings up other issues such as additional cost, and added internal resistance of system that also reduces the output voltage of the system. The extra barriers add to the cost of the system, increase electrical resistance, and reduce coulombic efficiency and power production. Further, the barriers are commonly not 100% efficient in exclusion of oxygen from anodic section due to crossover from cathodic compartment to anodic compartment.

In the industry, MFC treatment systems are only demonstrated at pilot scale, mainly because MFCs with two chambers and an electrolyte membrane are difficult to scale up in the structure. Using the membrane not only increases cost for configuring the system, but also has a problem in that the membrane may be contaminated during operation. This issue limits the application of MFCs for wastewater treatment, as the membrane easily gets fouled due to suspended solids and soluble contaminants found in wastewater. Adding to the problems, mechanical strength of the electrolyte membrane has to be high to endure scaled up pressures.

In view of the above, we see a need exists for a fuel cell/battery operated on organic matter and providing more practical voltage outputs. It would be desirable to have MFCs that are not reliant on oxygen and do not require membrane separation of the electrolyte. The present invention provides these and other features that will be apparent upon review of the following.

SUMMARY OF THE INVENTION

The present inventions are directed to biologic batteries or fuel cells (microbial fuel cells—MFCs) that employ a combination of half-cells providing improved voltage and amperage output over prior art cells. Generally, the MFCs include an anodic half-cell with a bioactive material generating an electron donor, and a cathodic half-cell wherein an alkaline metal cation is reduced. The MFCs can include, e.g., an anode assembly and cathode assembly in an electrochemical device comprising at least one halophile or halotolerant microorganism associated with the at least one anode, and at least one alkali metal ion insertion solid state cathode. Many of the present MFC configurations do not require a membrane separating the anode and cathode.

The MFC biologic battery can include, e.g., an electrolyte comprising an alkaline metal salt in solution; an anode comprising a first conductor associated with a bioactive material and immersed in the electrolyte, wherein the bioactive material is adapted to generate an organic electron donor molecule; and, a cathode comprising a second conductor in contact with the anode through an electrical conductor and in fluid contact with the electrolyte, wherein the cathode is adapted to reduce an alkaline metal ion from the electrolyte with an electron received from the anode.

The bioactive material of the MFC can be a biologic cell. Where the bioactive material is a microbe, the electrolyte can include a culture medium supporting metabolism of the microorganism. For example, the microbe can be a halophile, a thermophile, a facultative anaerobe, an acidophile, and/or the like. In many embodiments, the bioactive material is a halophile microbe or enzyme from a halophilic microbe. Exemplary microbes associated with the MFC anode can be a bacterium, a fungus, an alga, an archaebacterium, a protist, a plankton, a *Geobacter*, halophile, a *Halobacterium*, and/or the like.

The bioactive material can include an enzyme. The enzyme can obtain a reaction substrate from the electrolyte and catalyze generation of an electron donor product. For example, the enzyme can be a glucose oxidase, a lactate oxidase, a pyruvate oxidase, an alcohol oxidase, a cholesterol oxidase, a glutamate oxidase, a pyranose oxidase, a choline oxidase, a cellobiose dehydrogenase, a glucose dehydrogenase, a pyranose dehydrogenase, a fructose dehydrogenase, an aldehyde oxidase, a gluconolactone oxidase, an alcohol dehydrogenase, an ascorbate oxidase, a sulfide dioxygenase, a laccase, bilirubin oxidase, and/or the like. The electrolyte on an anode side of the battery have a fuel providing a substrate for the conversion by the microbe or enzyme. For example, the fuel can be a biologic waste, wastewater, compost, a food process waste, a sugar, an organic acid, a biopolymer, and/or the like.

The electrolyte can be tailored to promote the requirements of the elected half-cell reactions. For example, the electrolyte can be anaerobic, the electrolyte can include one or more alkaline metal salts, e.g., at concentrations ranging from, e.g., less than 100 mM to more than 1.5 M, from 250 mM to 1M, from 400 mM to 700 mM, or about 500 mM. The electrolyte can include one or more mediators, such as neutral red, $Mn^{4+}$, $Fe_3O_4$, $Ni^{2+}$, fluorinated polyanilines, anthraquinone-1,6-disolfonic acid (AQDS), and 1,4-naphthoquinone (NQ). The mediators can be coated onto a surface of the anode or in the electrolyte solution.

The MCF hardware can include a hermetically sealed casing with electrodes mounted therein. Such a casing can allow the electrolyte to be anaerobic. The casing container enclosing the electrolyte and the container can include an inlet port and outlet port allowing the electrolyte to be refreshed continuously or in a batch mode. The electrodes can include an anode and cathode comprising, e.g., a graphite, a solid support with a tethered enzyme, carbon paper, a biofilm, Pt, carbon, Ag, a noble metal, stainless steel, lead, gold, palladium, and/or combinations thereof. The anodic half-cell will typically include a bacterial catalyst. The cathodic half-cell can beneficially include an intercalation material of transition metal oxides, polyanions, or compounds that can reversibly intercalate alkali metal ion into their lattice. The intercalation material of the cathode can be in an alkali ion-deinserted state. The intercalation material can be selected from at least $Na_xMnO_2$, $MnO_2$, $NaCo_{1/3}Ni_{1/3}Mn_{1/3}PO_4$, $Na_2FeP_2O_7$, $NaVPO_4F$, $Na_3V_2(PO_4)_3$, $NaFePO_4$, $Na_3V_2O_{2x}(PO_4)_2F_{3-2x}$, $NaFe(SO_4)_2$, $NaCoO_2$, and cobalt oxide ($CoO_2$). Optionally, the cathode can be adapted to a conversion reaction function, e.g., using materials such as oxides, fluorides, oxyfluorides, sulfides, nitrides, phosphides, $FeF_3$, $CoF_2$, and/or the like. Optionally, the cathode further can employ metal-containing binary fluorides, metal-containing ternary fluorides, a complex fluoride, and/or an oxysalt.

There can be a porous membrane between the anode and cathode. The membrane pores can be adapted to allow migration of positively charged ions or molecules from the anodic side of the MFC to the cathodic side. For example, the membrane can be a Nafion™ or other perflouro-polymer. Alternately, there is no membrane in the electrolyte between the anode and cathode, with the electrolyte preferably anaerobic.

An exemplary MFC can have a first half-cell reaction at the anode wherein $CH_3COO^- + 4H_2O \rightarrow 2HCO_3^{2-} + 9H^+ + 8e^-$. A second half-cell reaction at the cathode be, e.g., $CoO_2 + xNa^+ + xe^- \rightarrow Na_xCoO_2$.

The inventions include methods of generating an electric current. For example, a DC current can be generated by providing a MFC, as described herein, e.g., having a bioactive material on the anode, an alkaline metal ion receptor cathode, and electrolyte comprising a feed stock substrate for the bioactive material. In the method, the feed stock in the electrolyte is metabolized by the bioactive material or enzymatically converted by the bioactive material into the organic electron donor molecule. Electric current is generated when the electron donor molecule donates an electron at the anode and it is conducted through a conductor to the cathode.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification, the singular forms "a", "an" and "the" can include plural referents unless the content clearly dictates otherwise. Thus, for example, reference to "a surface" can include a combination of two or more surfaces; reference to "bacteria" can include mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be practiced without undue experimentation based on the present disclosure, preferred materials and methods are described herein. In describing and claiming the present invention, the following terminology will be used in accordance with usage herein and the definitions set out below.

The terms "anodophiles" and "anodophilic microorganism" are used to refer to microorganism that transfer electrons to an electrode, either directly or by endogenously produced mediators. In general, anodophiles in the present MFCs are obligate or facultative anaerobes. The term "exoelectrogens" is also used.

The terms "cathodophiles" "cathodophilic microorganism" refer to microorganisms capable of preferentially colonizing the cathode, and the term "exoelectrotrophs" is used for microorganism capable of drawing an electron from cathode via a direct contact mechanism or self-secreted mediators to conserve energy for growth.

A "microbe" or "microorganism" can be any microscopic sized organism, including, for example, a bacterium, a fungus, an alga, an archaebacterium, a protist, a plankton, and the like. A microbe may be unicellular or multicellular.

A "MFC" (microbial fuel cell), as used herein includes batteries and fuel cells with a microbe or enzyme functionally associated with the anode. Many MFCs of the invention include a cathode adapted to reduce alkaline metal ions.

DETAILED DESCRIPTION

Figure 1:
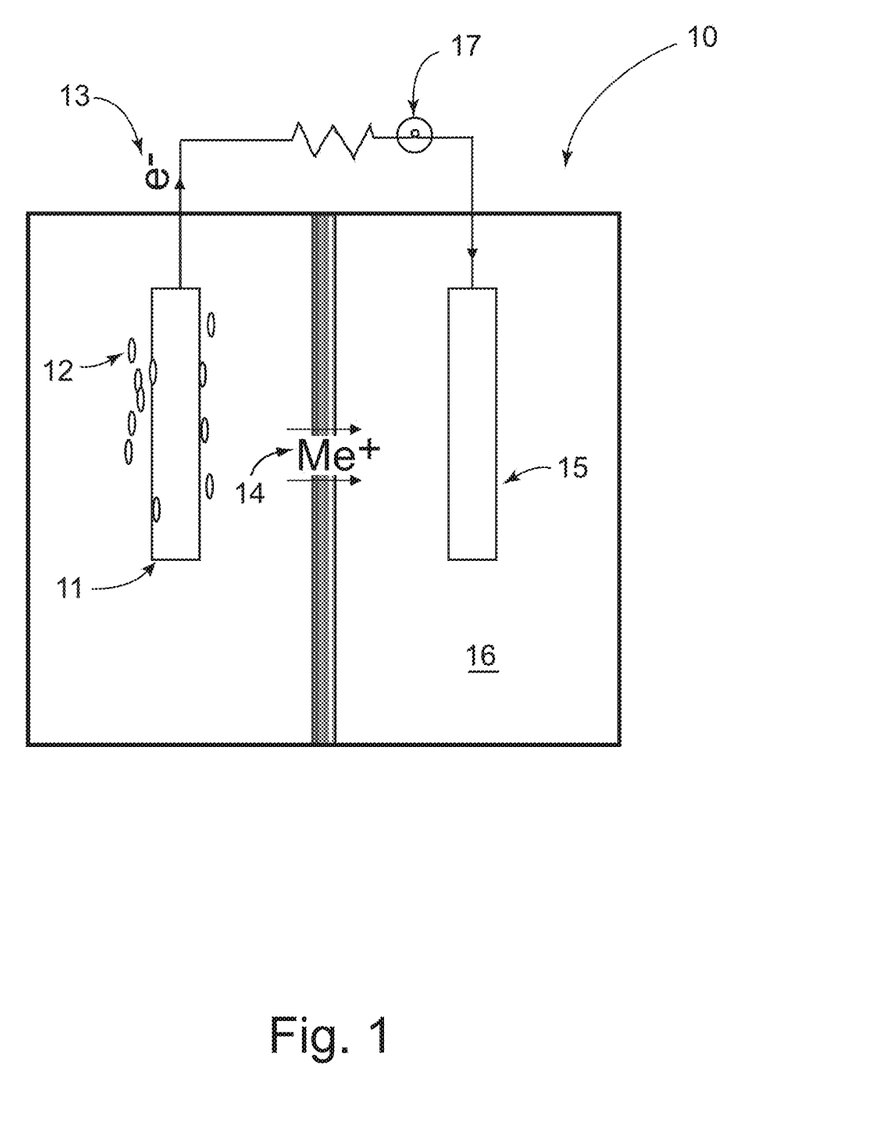
FIG. 1 is a schematic diagram presenting a generic fuel cell battery employing a bioactive material at the anode.

The biologic/alkali ion hybrid batteries (herein, MFCs) 10 generally include an anode 11 associated with a bioactive material 12 (e.g., enzyme or microbe). An oxidizable fuel is fed to the anode, where the bioactivity frees electrons 13 to the anode, while positive ions 14 (e.g., $Li^+$, $Na^+$, and/or the like) can migrate to the cathode 15 through an electrolyte 16. The electrons travel as a DC current, possibly through load 17 to the cathode.

In a typical configuration, the bioactive material is a microbe consuming an organic fuel and the electrolyte provides physiologic conditions favorable to the live cells. The consumption of the fuel frees, e.g., an electron and a positively charged ion. The electron is received by the anode, and the positively charged ion migrates through the electrolyte attracted by electrostatic forces to the cathode. In preferred embodiments, the electrolyte lacks oxygen and the microbe is an anaerobe suited to subsist, e.g., in an anaerobic and salty environment. In preferred embodiments, the positively charged ion is a proton or an alkaline metal ion.

Microbes can be selected and introduced to MFCs in the form of purified culture, enriched in a specified species of bacteria, genetically engineered, or mixed population, based on the desired MFC application. The use of selected strains may increase overall electron recovery. For example, *Geobacter* species are pili-producing microbes that can form thick (>50 mm) biofilms on the electrode, with the pili allowing cells a substantial distance from the anode to contribute to current production. While the conductive pili are responsible for electron transfer through the bulk of the biofilm, these microbe species also benefit from c-type cytochromes on their outer surface facilitating electron transfer between the biofilm and the anode surface.

In a preferred embodiment of the fuel cells/batteries (MFCs), organic molecules are metabolized under anaerobic conditions at the anode releasing a metal ion (such as $Li^+$). The metal ion migrates to the cathode providing a greater voltage potential between the anode and cathode than prior art MFCs.

A number of methods and compositions are discussed in the Summary of the Invention and further details are provided herein and in the Examples section. As would be readily appreciated by the skilled person, the disclosures can be read in combination.

Anodes of the invention receive molecules or ions relatively predisposed to oxidation (low redox potential) and receive an electron that can be passed on to a molecule of higher redox potential at the cathode, providing a useful electric current. The anodes can simply be conductors to receive electrons, or can provide a substrate for enzymes and/or microbes generating the low redox ions or molecules. The anode can be bathed in the electrolyte and in electrical contact with the cathode through a conductor.

The anode can be fabricated from any appropriate conductive materials. Exemplary materials can include graphite, Pt, carbon, Ag, a noble metal, a conductive ceramic, stainless steel, lead, gold, palladium, and or the like. The anode can act as a solid support with enzyme tethered to the surface and/or as a surface for growth of a biofilm. In certain cases, the anode can be textured or laminated to increase the available surface area.

Anodes can have the microbes in direct or indirect contact with their surface. The microbes can be any suitable to the electrolyte and ambient conditions. For example, the microbes generating the feed of low redox metabolytes can be halophiles, anaerobes, halophilic anaerobes, thermophiles, facultative anaerobes, halotolerant, polyextremophilic microorganisms, psychrophilic microbes, alkaliphiles, acidophiles, and/or the like.

Anodes can have enzymes in direct or indirect functional contact with their surface. The enzymes can be in a proximity to the electrode wherein the enzymatic reaction products can interact functionally in the cell. The enzymes should be appropriate to the intended feed stock of molecules in the electrolyte. For example, the enzymes can include glucose oxidases, lactate oxidases, pyruvate oxidases, alcohol oxidases, cholesterol oxidases, glutamate oxidases, pyranose oxidases, choline oxidases, cellobiose dehydrogenases, glucose dehydrogenases, pyranose dehydrogenases, fructose dehydrogenases, aldehyde oxidases, gluconolactone oxidases, alcohol dehydrogenases, ascorbate oxidases, sulfide dioxygenases, laccases, bilirubin oxidases, and/or the like. It is further desirable that the enzymes are engineered or naturally adapted to extreme conditions that may be found in a battery, such as high temperatures, pH extremes, high salt conditions, and the like.

Cathodes of the MFCs receive electrons from the anode and reduce a molecule/ion having a relatively high redox potential. For example, a half-cell reaction at the anode can generate both an electron and a positively charged reaction product. The vast majority of electrons travel through the conductor to the cathode, due to the far lower electrical resistance of the conductor as compared to the electrolyte. The positively charged reaction product can be electrostatically driven to migrate through the electrolyte (optionally, also a permeable membrane) to the cathode, where it is reduced by an electron.

As with the anodes, the cathode can be a simple conductive material, e.g., such as graphite, Pt, carbon, Ag, a noble metal, a conductive ceramic, stainless steel, lead, gold, palladium, and or the like. In a desirable aspect, the cathode can comprise an intercalation material of transition metal oxides, polyanions, or other compounds that can reversibly intercalate an alkali metal ion into their lattice. Materials that may function to intercalate metal ions at the cathode can include, e.g., $Na_xMnO_2$, $MnO_2$, $NaCo_{1/3}Ni_{1/3}Mn/PO_4$, $Na_2FeP_2O_7$, $NaVPO_4F$, $Na_3V_2(PO_4)_3$, $NaFePO_4$, $Na_3V_2O_{2x}(PO_4)_2F_{3-2x}$, $NaFe(SO_4)_2$, $NaCoO_2$, cobalt oxide ($CoO_2$), and/or the like. In certain embodiments, the cathode material is in an alkali ion-deinserted state.

Optionally, the reactions at the cathode can include conversion reactions wherein the positive ion from the anodic reaction exchanges for a metal ion at the cathode. In such cases, the positive ion can be, e.g., a $Li^+$, $Na^+$, or the like, e.g., from the electrolyte. The materials converted at the cathode by the positive ions can be, e.g., metal oxides, fluorides, oxyfluorides, sulfides, nitrides, phosphides, $FeF_3$, $CoF_2$, and/or the like.

As with the anodes, there can be benefits in capacity, current, and voltage when the surface area of the cathode is increased. For example, the cathode can be textured, laminated, an open cell foam, particulate, and/or the like.

Electrolytes in the MFCs can be any appropriate, e.g., to the particular combination of biologic action at the anode and cation reduction at the cathode. The electrolyte can include, e.g., culture media feed stock for the bioactive feature, salts, mediators, and the like.

The choice of electrolytes can be strongly influenced by the nature of the bioactive feature at the electrode. Many biomolecules and microbes may require specific feed stocks and can require specific conditions of ionic strength, specific nutrients, temperature, environmental redox conditions, pH, and/or the like.

The feedstock in the electrolytes can be highly controlled and purified, or the systems can operate on crude waste materials. Microorganisms (or combinations of microorganisms) can often receive a complex feed stock (e.g., household waste water). They can employ diverse enzymes to, e.g., degrade diverse sugars and polymers into organic acids and protons. However, there are advantages (e.g., fewer process cycle issues) where the microbes are fed a more well-defined feed stock. In other embodiments, enzymes (or combinations of enzymes) can typically receive relatively more purified feed stock, such as sugars or alcohols to produce the low redox molecules for the anode and cations for the cathode.

Because anaerobic reactions can typically offer higher voltage potentials across the electrodes and reaction kinetics it can be preferred to configure the MFCs to exclude oxygen from the electrodes and/or electrolyte. The electrolyte may be sparged with gasses free of oxygen or the electrolyte may be degassed prior to assembly of the cells. In many cases, particularly where the microbe is a facultative anaerobe, any residual oxygen in the electrolyte can be rapidly consumed during metabolism of the feed stock.

To generate electricity using a microbial fuel cell, electrons produced from the energy metabolism of microorganisms should be transferred to an electrode. Electron transfer can happen directly with anionic metabolic products contacting the anode, directly through in situ-produced microbial nano-wires (pili), or indirectly through added electron shuttles (mediators) that receive a charge from a metabolic product and pass it on to the anode.

In cases where microbes are unable to directly transfer electrons to the anode, mediators such as neutral red, $Mn^{4+}$, $Fe_3O_4$, $Ni^{2+}$, fluorinated polyanilines, anthraquinone-1,6-disolfonic acid (AQDS), 1,4-naphthoquinone (NQ) can be either coated on the anode surface, or added to the electrolyte.

The electrolyte can include organic molecules (such as sugars, carbohydrates, fatty acids, and the like) at a concentration adequate to meet the demand for metabolic products required in the desired current output; and to feed the microbes, as necessary. Further, the electrolyte can include other nutrients typically found in media used to grow the microbes. For example, the electrolyte can provide proteins/peptides/amino-acids; essential metals and minerals; and buffering agents. Where the bioactive material is an enzyme, the electrolyte may include components that help enhance the activity of the enzyme, e.g., buffers and cofactors.

The electrolytes can provide a source of the positive ions that are attracted to the cathode to take part in the cathodic half-cell reaction. These cations can be those released by the bio-metabolism or can simply be positive charge carriers. For example, the electrolyte can include mediators that receive a positive charge at the anode and carry it to the cathode. The mediator can be limited in supply and ultimately exhausted, or take part in regeneration reactions that render them recyclable.

MFC structures play important roles in providing an environment conducive to efficient current generation in the MFCs. The MFCs can include a housing to fluidly seal the electrolyte, mount the electrodes, seal out undesirable gasses, allow replenishment of feed stock, and allow removal of waste materials.

Figure 2:
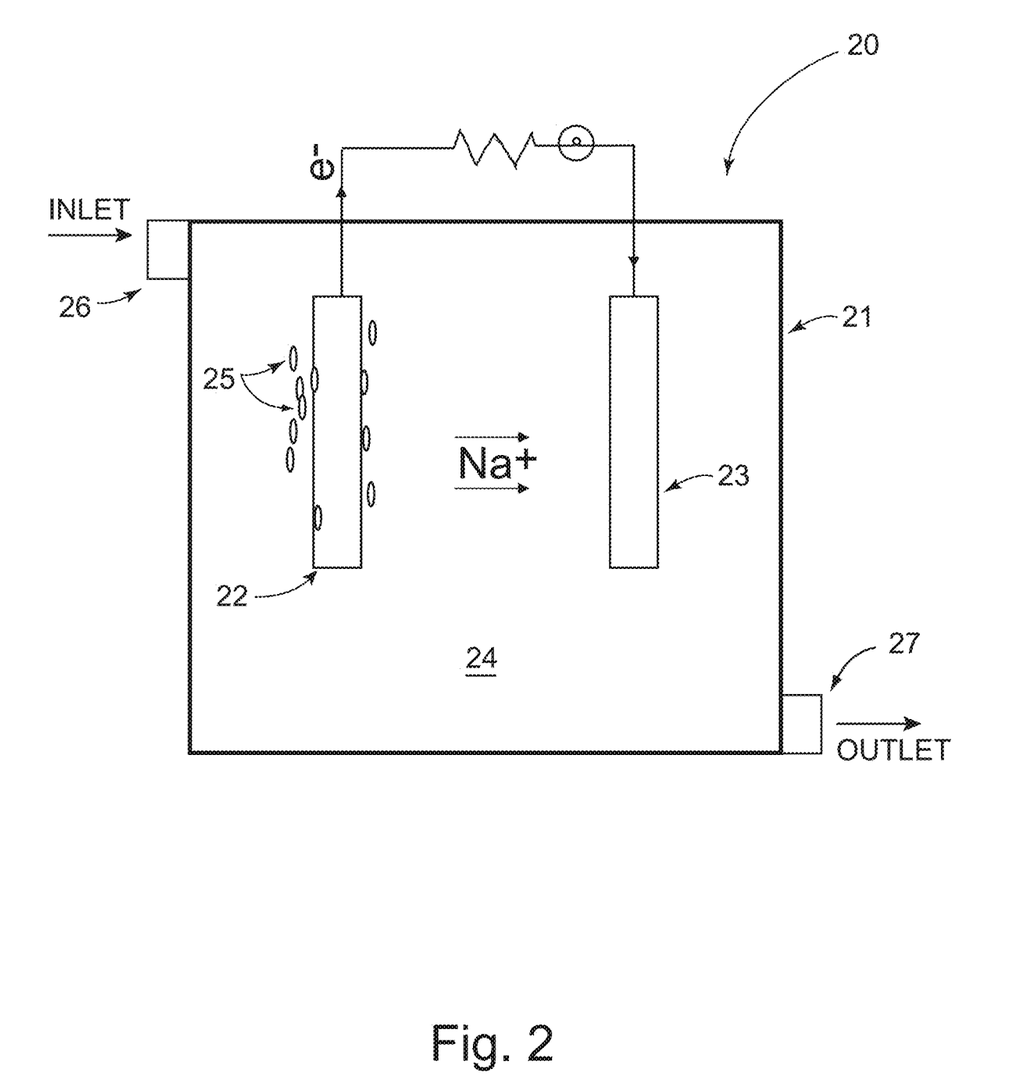
FIG. 2 is a schematic diagram of a MFC employing microbes at the anode. The MFC is without a membrane and has an inlet and outlet allowing battery feed stock and other electrolyte components to be refreshed.

In one arrangement (see, FIG. 2), the MFC 20 includes sealed housing 21 with anode 22 and cathode 23 in electrolyte 24. Microbes 25 are in the electrolyte and can form a biofilm on the anode surface. The MFC can be arranged to provide replenished electrolyte flowing in from inlet 26, while waste flows out through outlet 27. In operation, the microbes can be continuously or intermittently fed organic feed stock to produce negatively charged metabolic products. The metabolic products can donate electrons to the anode. Positively charged metabolic products can migrate directly to the cathode to receive electrons and complete the circuit.

Figure 3:
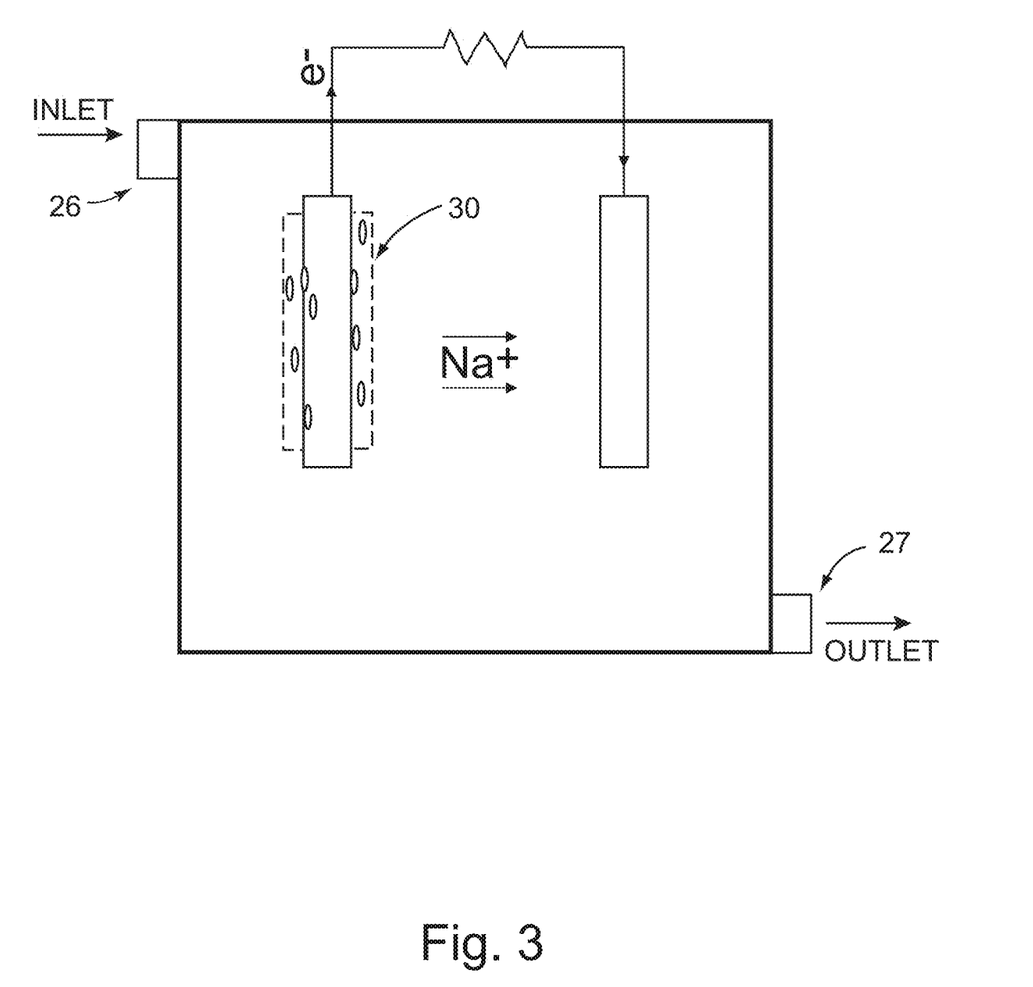
FIG. 3 is a schematic diagram of a MFC employing enzymes at the anode. The MFC is without a membrane and has an inlet and outlet allowing battery feed stock and other electrolyte components to be refreshed.

In a similar arrangement, the fuel conversion at the anode is catalyzed by one or more enzymes. There can be microbes in the electrolyte generating substrate for the enzyme or the substrate can be delivered (fully or partially purified) without the aid of microbes. As shown in FIG. 3, the enzyme 30, is typically bound to the anode or present in a matrix at the anode. This ensures that the negatively charged metabolic product attains higher concentrations at the anode. To prevent the growth of microorganisms on the cathode surface, sometimes the cathode is coated with an cation permeable protective layer.

Figure 4:
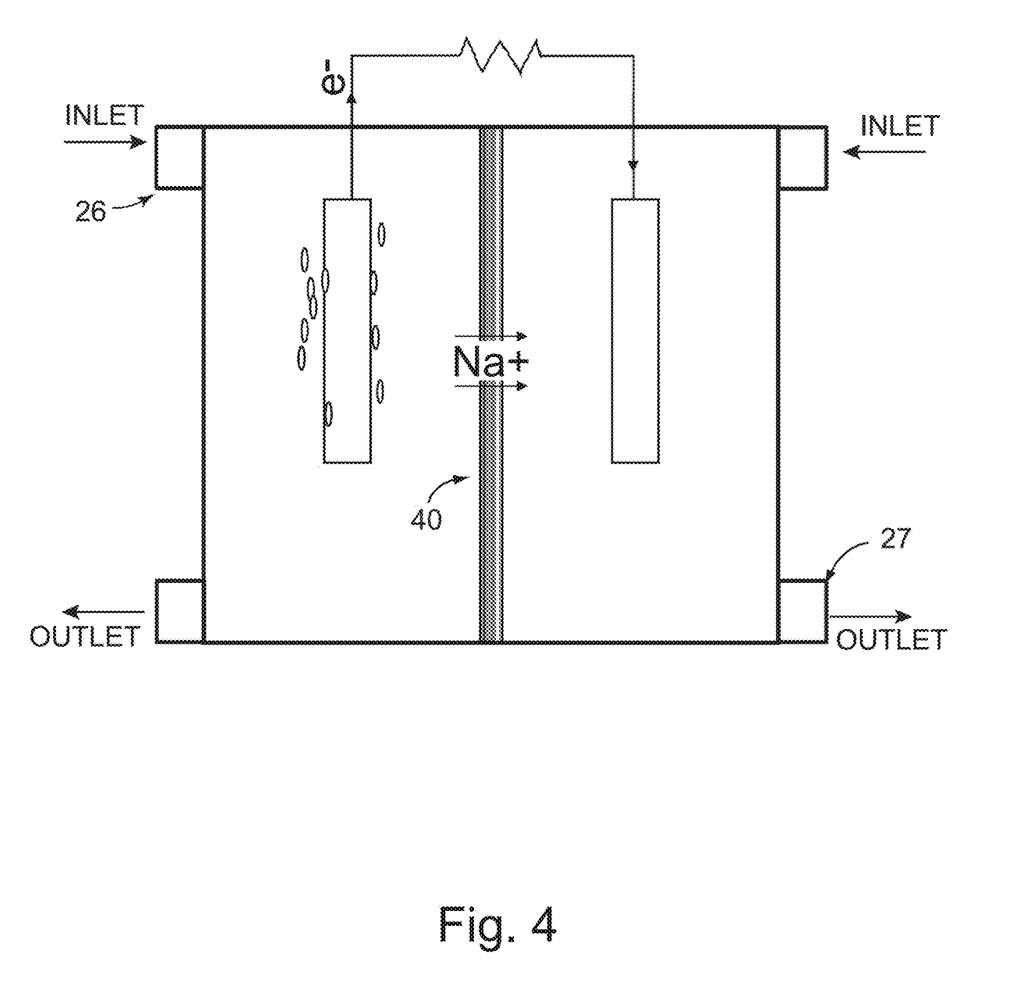
FIG. 4 is a schematic diagram of a MFC employing microbes at the anode and having a membrane between the anodic cell and the cathodic cell.

In certain embodiments, there can be a porous membrane between the anode and cathode, as shown in FIG. 4. The membrane 40 can have a porosity that allows protons or alkaline metal ions to pass through, e.g., but not allow substantial diffusion of other electrolyte constituents (e.g., microbes, fuel molecules, negatively charged metabolic products, or enzymes) pass through. Alternately the membrane can be configured to also allow metabolic wastes to pass through, e.g., to be expelled through outlet 27.

Figure 5:
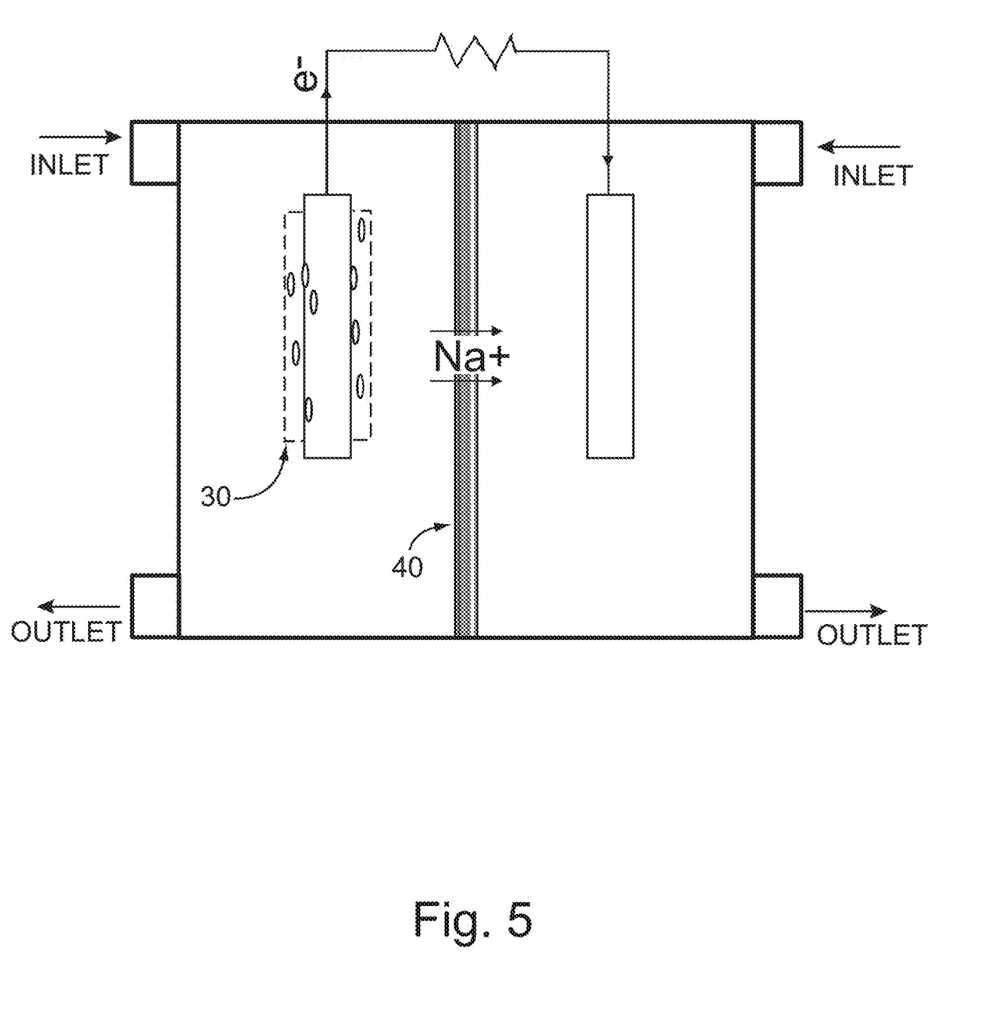
FIG. 5 is a schematic diagram of a MFC employing enzymes at the anode and having a membrane between the anodic cell and the cathodic cell.

In another iteration of the MFCs, the bioactive material on the anode is an enzyme 30, as shown in FIG. 5. Transit of ions and molecules between the anodic half-cell and cathodic half-cell can be moderated by membrane 40.

The membranes can be any with appropriate electrical resistance and pore size for a particular application. Typically the membrane is made from a perflorinated composition having a pore size allowing protons or alkaline metal cations to pass, but not larger ions or molecules. Preferred membranes can be of a polytetrafluoroethylene (PTFE) or sulfonated polytetrafluoroethylene (PFSA), a fluoropolymer copolymer, carbon paper, or the like.

EXAMPLES

The following examples are offered to illustrate, but not to limit the claimed invention.

Example 1—MFC Areas of Improvement

The efficiency of energy recovery in MFCs is significantly reduced by two main undesirable phenomena. The first is voltage loss from reduction of $O_2$ at the cathode, which is exacerbated by MFC operating conditions such as atmospheric pressure, ambient temperature, and an aqueous electrolyte at near neutral pH. Another phenomenon is diffusion of dissolved $O_2$ into the anode compartment, allowing formation of aerobic biomass and oxidation of organic matter without energy production. Accordingly, we have seen it would be an advance in the art to provide improved microbial chemical to electrical energy conversion.

The present work introduces a new microbial electrochemical device for energy recovery where a key difference is the use of alkali metal ion insertion solid-state cathode to replace the oxygen gas cathode of a MFC. Specific types of microorganisms are being used to open the possibility to use a completely new and $O_2$-free class of cathodes in MFCs. Operation of the anode is similar to that of an MFC anode, but operating in a new combination with a cathode similar to that of an alkali metal ion battery. Such novel MFCs have the added benefit of possibility eliminating the requirement of having a membrane between half-cells; thereby forgoing the issues caused by oxygen cathode, as well as membrane, in conventional MFCs.

Example 2—Components of the MFCs

Microorganisms—specific classes of microorganism, e.g., adapted to high salinity, can be used in the anode compartment to catalyze the oxidation reaction. Haloterants and halophiles organism including bacteria, archaea, yeasts, algae and fungi, and halophyte plants can produce stable enzymes capable of functioning under high concentrations of salts (e.g., as found in many battery electrolytes). These enzymes can also be extracted and used as catalysts for biofuel cells.

Some of the microbes in the MFCs can be adapted to several extremes at the same time (e.g., multi-resistant or polyextremophilic microorganisms). For example, halophilic-psychrophilic, halophilic-mesophilic, and halophilic-moderately-thermophilic microbes, can live in the conditions of 3-30% (w/v) NaCl, and temperature <10, 15-40, and 50-60° C., respectively. Another example can be acidophilic halophilic microbes, such as *Halarchaeum acidiphilum* that grow in the pH range 4 to 6, with an optimum at pH 4.4 to 4.5 and 210 to 240 g/L NaCl. Such multi-resistant organisms can be specifically useful to diversify the operation conditions of our microbial fuel cells. For example, using halophilic psychrophilic and halophilic thermophilic microbes can widen the operational temperature range in a microbial fuel cell. And, acidophilic halophilic microbes can adapt and thrive in naturally low pH conditions that are found during proton generation in the anodic compartment during fuel oxidation. Optionally, issues of low pH in the fuel cell can be addressed by regulation and adjustment to optimal conditions for the type of organism employed in the cell. This can be done by addition of alkaline solutions, e.g., in a flow or batch system, to replace the solution in the fuel cell when the pH is out of the optimum conditions.

Halophiles and halotolerant microorganisms are two suitable domains of extremophilic microorganisms for the presented MFCs. Such microorganisms able to grow in the presence of salt are found in all three domains of life: Archaea, Bacteria, and Eukarya. Halophiles require high salinity (NaCl and other salts) to survive. Whereas halotolerants can grow under saline conditions, but do not require elevated concentrations of salt for growth. Halotolerant species tend to live in areas such as hypersaline lakes, coastal dunes, saline deserts, salt marshes, and inland salt seas and springs. Halophiles can be found in environments, e.g., with a concentration of salt five times greater than the salt concentration of the ocean, such as saline soils, hypersaline lakes, solar salterns, and in evaporation ponds. Extreme halotolerants are able to grow above approximately 15% (w/v) NaCl (2.5 M). Halophiles are categorized based on the amount of salinity required into the following groups: mild, moderate, and extreme halophiles grow optimally in media with low 0.2 to 1 M (1-6%), moderate 1 to 2.6 M (6-15%), and high 2.6 to 5.1 M (15-30%) salinities, respectively.

The metabolic diversity of halophiles is very wide: oxygenic and anoxygenic phototrophs, aerobic heterotrophs, fermenters, denitrifiers, sulfate-reducers, and methanogens. Obligate anaerobic halophiles are called halanaerobiales. Some members of Halobacteriaceae in the domain of Archaea are facultative anaerobes. Such microbes offer options for MFCs to be used in a variety of environments, and in cooperation with a variety of cathodic half-cells.

Generally, halophiles and halotolerants use two methods of survival in extreme hypersaline conditions to balance the osmotic pressure caused by high extracellular salt concentrations: 'salt-in' and 'organic solutes-in' strategies. Both strategies involve maintaining osmolarity within the cell. In the 'salt-in' strategy, cells maintain high intracellular salt concentrations and in 'organic solutes-in' method cells accumulate organic compatible solutes, e.g. proline, glycerol, glycine-betaine, trehalose, and sucrose.

As extremophilic organisms have strong resistance to diverse harsh conditions, they are subject to investigation in several basic research areas, as well as applied and biotechnological areas, including industrial applications. Examples include production of salt-tolerant enzymes, biopolymers, and biosurfactants. Other uses are related to environmental applications such as bioremediation processes, wastewater treatment, and power generation in microbial fuel cells. Yet their possible applications have not been fully explored by others. There are advantages in growing cultures of halophiles and halotolerant microorganisms at industrial scale such as their high growth rates using simple substrates such as starch or acetate as carbon sources, ease of contamination prevention with other organisms due to high salt concentrations in their culture media.

The application of halophilic microorganisms in the anodic compartments of MFCs can allow employment of conventional oxidants, such as oxygen, air, or potassium ferricyanide, in the cathode compartments. Examples include: halotolerant microorganisms, anaerobic haloalkaliphilic bacteria, halophile archaea, and slightly halophilic bacteria. Other common oxidants are occasionally mentioned, for example in one study denitrifying halotolerant bacteria is used to reduce nitrate and perchlorate. However, we have discovered substantial benefits can be obtained using such half-cell arrangements in combination with alkali-metal ion cathodes.

It is notable that another advantage of using extremophiles in the present MFCs is that the extreme environments of high salinity, pH extremes, and/or temperature extremes tends to prevent the system from being overrun by undesirable contaminant microbes.

Example 3—Cathodes

Identification of a stable solid-state electrode with suitable electrochemical potential to replace oxygen or air cathodes in MFC is a feature of this invention. Alkali metal ion (such as lithium and sodium ions) cathode materials have been used in lithium, sodium, and potassium ion batteries (LIB, SIB, and PIB, respectively). Among the alkali metals, sodium is the most earth-abundant element, and naturally high concentration of it can be found on seawater and some lakes. So, in many applications it is more cost-effective to use sodium-based cathode materials.

In many cathodes, the electrode structures are adapted to host the alkali ions. Alkali ion insertion and extraction in the electrode matrix is possible, or the alkali metal and the host metal form an alloy, or redox or conversion reaction of host with sodium. The cathode usually needs to be chemically stable at the operating pH of the aqueous electrolyte, and dissolution of materials should not occur. Some examples of cathode materials where sodium as the alkali metal of choice include but are not limited to transition metal oxides (e.g., cobalt oxide, nickel oxide, manganese oxide), transition metal phosphates (e.g., iron phosphate), transition metal sulfates (e.g., iron sulfate), transition metal fluorides, transition metal oxyfluorides, carbon monofluoride ($CF_x$), and/or the like.

Examples of the mechanisms by which a material can act as cathode for alkali metal ion insertion include but not limited to:

(1) Intercalation-deintercalation mechanism. Transition metal oxides, polyanions (e.g. phosphates and sulfates), and other compounds that can reversibly intercalate alkali metal ions into the lattice without destroying the crystal structure, have been explored. The metal oxides, phosphate, sulfates, and so on can be binary or ternary or even more complex. Some examples of many cathodes from SIBs are $Na_xMnO_2$, $MnO_2$, $NaCo_{1/3}Ni_{1/3}Mn_{1/3}PO_4$, $Na_2FeP_2O_7$, $NaVPO_4F$, $Na_3V_2(PO_4)_3$, $NaFePO_4$, $Na_3V_2O_{2x}(PO_4)_2F_{3-2x}$, and $NaFe(SO_4)_2$. In the present application, these materials are typically being used in their sodium-deinserted (partially or completely desodiated or without Na) state.

The host compounds, such as $MnO_2$, operate on the $Mn^{4+}/Mn^{3+}$ redox couple on insertion of either $Na^+$ ions. Sodium insertion potential in these materials is known to be ≤3.5 V vs. $Na^+/Na$ or ≤0.8 V vs. SHE. At pH=7, water does not decompose in voltages ranging from −0.41 to +0.81 V vs SHE, so the solvent will be stable. The cathode potential is higher than the value for other electron acceptors commonly present in anaerobic environments (such as $SO_4^{2-}$ and $CO_2$), and is also very close to oxygen reduction potential (0.81 V vs. SHE or 3.51 V vs $Na^+/Na$ at pH=7). So, sodium ion, when electrochemically inserted in these host matrices, can be almost as strong oxidizer as oxygen. Moreover, host compounds for alkali metal ion insertion remain in the solid state in water as shown by research on aqueous sodium ion batteries. This can be advantageous over some of the previous cathode materials in MFCs, where upon reduction the cathode material becomes soluble, which might be harmful to the microorganisms.

(2) Redox or "conversion" reactions with alkali metal ion. In this category, the cathode consists of elements with high electronegativity (such as O, S, F, etc.), and alkali metal ions have high affinity to form bonds (reversible or irreversible) with such elements. These cathodes can be in various compositions and might contain transition metals and/or carbon particles. These cathodes may or may not be electrochemically regenerated. Some examples are shown by the reactions:

$CF_x + xLi^+ + xe^- \rightarrow C + xLiF$ and $CF_x + xNa^+ + xe^- \leftrightarrow C + xNaF$ The conversion reaction is a general phenomenon and is applicable to oxides, fluorides, oxyfluorides, sulfides, nitrides, phosphides, etc. Some examples of metal-containing cathodes in this category are $FeF_3$ and $CoF_2$. More complex compounds such as metal-containing binary, ternary, and complex fluorides and oxysalts can be used as cathodes as well.

The alkali metal ion insertion or conversion reactions mentioned in the two categories, occur at high potentials (as high as ≈1.25 V vs. SHE).

Example 4—Anodes

The potential of the anode is set by the oxidation of the substrate. Thus, the anode side of the current system can operate similarly to a conventional MFC wherein bacteria oxidize an organic compound, and transfer electrons to the anode.

The materials which can be used for anode in this invention may be the conventional anodes for microbial or biofuel cells which are used in prior art. For example, conventional graphite or carbon.

Example 5—Membranes

In MFCs outlined by this invention, the separation between the anodic and cathodic compartments is not required because oxygen is completely eliminated from the system. So, this MFC can perform as a membrane-less system. Elimination of membrane from MFC will increase its power output (by lowering the internal resistance), reduce its cost, and improve its design as discussed previously. In a conventional MFC system, a drawback in eliminating the proton exchange membrane (PEM) is that coulombic efficiency drops due to increased oxygen diffusion from the cathode. In contrast, in our inventive anaerobic system this problem is eliminated.

Preferably, the electrolytes in the anode and cathode compartments are the same, and anode and cathode are placed in the same compartment but based on the application, if separation between cathodic and anodic chambers is preferred, any conventional membrane or separator, including Nafion™ membrane, can be used. For example, although the preference is to have aqueous electrolyte in both anodic and cathodic compartments, in some embodiments, the electrolyte in cathode compartment can be a non-aqueous solution that contains the alkali metal ion along with other cations and anions. In another example, the electrolyte in anodic and cathodic compartments might be both aqueous, but with different constituents from each other. In such cases a separator can be included in the design of the MFC to separate the anodic and cathodic chambers.

Example 6—Fuel and Other Additives

The fuel can be any of the substances known in the art, e.g., to be oxidizable by microorganisms from halotolerant and/or halophile groups. The fuel of choice is delivered in a suitable medium or solvent compatible with microorganisms' metabolism. A preferred medium is aqueous and has high salinity in the range suitable for the elected microorganisms. The medium or solvent may be adjusted to be compatible with microorganism metabolism, for instance, if necessary, by adjusting pH through addition of a buffer to the medium or solvent, addition of growth-promoting or growth-inhibiting additives or supplements such as nutrients, cofactors, or vitamins.

Other parameters such as temperature, osmolarity, and ionic strength of the medium in the MFC reactor can be optimized according to requirements for the particular microorganism and MFC performance.

Example 7—Design and Other Details

In the presence of ambient oxygen (e.g., outside of outer space applications), the anode and cathode are preferably housed in a common hermetic enclosure. The system may be maintained in anaerobic conditions by flow of a gas such as nitrogen, carbon dioxide, argon, or mixture of gases.

Other than active material such as mentioned examples, cathode might contain conductive material such carbon, binder material such as binding polymer, and protective coatings. The cathode can be in a liquid or semi-liquid form. In such case the said cathode and its electrolyte are combined and mixed together, are called catholyte.

To prevent the growth of microorganisms on the cathode surface in the membrane-less embodiments of the presented system, a protective layer can be added or coated on the cathode that still allows the diffusion of all species except the microorganism to the cathode catalyst and conductive matrix. For example, this layer could be an anti-bacterial coating, or filters with proper pore sizes to exclusively exclude the microorganisms present in the system.

The anode and the cathode can have various shapes, structures, sizes, and architectures. They can be plates, meshes, brushes, etc. Also, anode and cathode may be positioned in various ways, and distances in relation to each other.

Optionally, the MFC system includes more than one anode and/or more than one cathode. The MFC system may include multiple cells in series, e.g., resulting in a higher voltage output. The number and placement of one or more anodes and/or one or more electrodes may be considered in the context of the particular application.

A MFC according to this invention might be configured for operation in batch mode and/or in continuous flow mode. If the medium containing the fuel material is delivered to microbes on the anode periodically, the system is said to operate in batch mode. If the medium containing the fuel is delivered to the microorganisms continuously over a period of time, the system is said to operate in flow mode. Similarly, the medium depleted of fuel may be removed periodically or continuously. For example, the MFC can be designed to include appropriate inlet and/or outlets for delivery of a medium containing and/or depleted of fuel to microbes.

In addition to the fuel delivery inlet/outlet channels, other channel(s) may be included to allow and/or regulate flow of materials into and out of the reaction chamber(s). For example, different channels may be included to allow for inflow/outflow of liquid at the cathode and anode. Further, a channel may be included to allow for outflow of a gas generated at each of electrodes. Valve(s) may be included to regulate flow of materials into and out of the reaction chamber(s). Also, pump(s) may be provided for enhancing flow of liquid or gas into and/or out of a reaction chamber(s).

Example 8—MFC Kinetics

Alkali metal ion host compounds have been studied in the form of aqueous alkali ion batteries such as aqueous sodium ion batteries. When the sodium ions intercalate into the cathode, the region closest to the cathode is replenished, while slowing mass action of further intercalation. In order to overcome the negative effects of slow sodium ion diffusion towards or into the cathode, it is important to maintain high concentration of sodium ions in the system. By doing so, the ion conductivity of MFC can be much higher, and internal resistance of the system reduced for a higher output voltage.

A high salt concentration generally has a positive effect on the performance of MFCs. The power production in an MFC has shown an increase of up to 85% when sodium chloride electrolyte concentration was raised from 100 to 400 mM, due to the increase in the ionic strength of the solution. Electricity generation by slightly halophilic bacteria was also increased due to lower solution internal resistance in solutions containing up to 1.5 M NaCl. Higher ionic strength is speculated to enhance the power production even more, but bacteria that are not adapted to higher salinity cannot be used as the stress induced by the high salinity reduces the metabolize efficiently. Solving these problems is our system combining suitable halotolerant or halophile microorganisms in anode, and sodium ion (or other alkali metal ions) cathodes. Both half-cells can perform optimally under high salt concentration (high ionic strength) and the internal resistance of the total system will be minimized as a desirable side effect.

High salt concentrations decrease the internal resistance of the MFC system as the resistance of the electrolyte is the reciprocal of the electrolyte conductivity. The external voltage of the MFC, V, can be described as follows:

$$V = E_C^0 - E_A^0 - 1 \times R_{m,C} - 1 \times R_{c,C} - 1 \times R_{m,A} - 1 \times R_{c,A} - 1 \times R_{int}$$

$E_C^0$ and $E_A^0$ are standard potentials at the cathode and anode, respectively, and $E_C^0 - E_A^0$ is the cell voltage maximum. $1 \times R_{m,C}$ and $1 \times R_{c,C}$ are overpotential losses at cathode due to mass and charge transfer, respectively. Similarly, $1 \times R_{m,A}$ and $1 \times R_{c,A}$ are overpotential losses at anode due to mass and charge transfer, respectively. Finally, $1 \times R_{int}$ is the sum of overpotential losses owing to anodic, cathodic, membrane, external connections (wire conductors), the electrolyte resistances, as well as all interface resistances.

To maximize the attainable external voltage, the overpotential losses need to be minimized. A key factor in minimizing the charge transfer (electron transfer) overpotential ($\eta_c$) is to maximize exchange current density ($i_0$):

$$\eta_c = A \ln\left(\frac{I}{i_0}\right)$$

Similar to reductive potential and reduction activation energy, exchange current density is an intrinsic property of a heterogeneous electrochemical reaction, and is crucial in controlling the performance of a fuel cell electrode. It is vital to make exchange current density value as high as possible. A typical $i_0$ value for platinum oxygen cathodes would be about $10^{-4}$ A cm$^{-2}$. The reported values for alkali metal ion cathodes varies based on the type of the ion insertion host, as well as the alkali ion. For comparison, the values, for lithium ion cathodes, are in the order of $10^{-3}$ to 1 A cm$^{-2}$ in non-aqueous solutions. We envisioned that overpotential due to electron transfer in cathode will be improved significantly with the new proposed cathode.

The difference in mass transfer limitations between oxygen and alkali metal ion cathodes can be understood by comparing their limit of solubility in water: the concentration of dissolved oxygen in water does not exceed the range of 0.006 and 0.04 g/L (0.4 and 2.5 mM) and, depending on the partial pressure and temperature so slow mass transfer rate is also a limiting factor. Since oxygen in a gas state should be dissolved into the electrolyte to receive electrons at an electrode, the potential difference between the cathode and the anode can be changed according to the reactivity of oxygen provided to the surface of electrode. Whereas alkali metal ions such as Na$^+$ as the oxidizer can be provided in an aqueous solution in the form various salts with high concentration. Sodium chloride dissolution limit in water, as an example of a naturally abundant salt in lake and sea water, is about 360 g/L (>6 M) in 1 atmosphere pressure, and temperatures higher than 0° C. It is worth mentioning that diffusion coefficients for alkali metal ions and oxygen gas, in water at 25° C., are similar, and in the order of $10^{-5}$ cm$^2$/s.

Overall, the attainable voltage is expected to improve at least through decrease of charge transfer and mass transfer overpotential at cathode, as well as decrease of internal overpotential through higher ionic conductivity of the solution in both cathode and anode. It should be noted that the presence of a membrane, and its interfaces also contributes to internal resistance. As mentioned before, the present systems in some applications eliminates the need for a membrane, due to use of the same electrolyte composition at anodic and cathodic compartments. Therefore, in such MFCs another source of internal overpotential is also omitted, contributing to overall higher attainable output voltage (V), and power (P):

$$P = I \times V$$

Although the reaction in cathode, and overall internal resistance of cell benefit from higher salinity, this is not the case for most of microorganisms. In fact, most known microorganisms can only tolerate low saline solutions. The extremophile groups can solve many of these problems. These bacteria or archaea (Prokaryotes) can thrive in solutions having high salinity. Further, using extremophiles, new classes of oxidizers can be introduced to eliminate the need for anode-fouling, slow-reducing oxygen, while the separator membrane is excluded.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A biologic battery comprising:
   an electrolyte comprising an alkaline metal salt in solution;
   an anode comprising a first conductor associated with a bioactive material and immersed in the electrolyte, wherein the bioactive material is adapted to generate an organic electron donor molecule;
   a cathode in fluid contact with the electrolyte and comprising a second conductor in contact with the anode through an electrical conductor, wherein the cathode is adapted to reduce an alkaline metal ion from the electrolyte with an electron received from the anode.

2. The battery of claim 1, wherein the bioactive material is a halophile microbe or enzyme from a halophilic microbe.

3. The battery of claim 1, wherein the battery is hermetically enclosed and the electrolyte is anaerobic.

4. The battery of claim 1, wherein the bioactive material is a microorganism and electrolyte comprises a culture medium supporting metabolism of the microorganism.

5. The battery of claim 1, wherein the bioactive material is a cell or an enzyme.

6. The battery of claim 5, wherein the cell is selected from the group consisting of: a halophile, a thermophile, a facultative anaerobe, and an acidophile.

7. The battery of claim 5, wherein the enzyme is selected from the group consisting of a glucose oxidase, a lactate oxidase, a pyruvate oxidase, an alcohol oxidase, a cholesterol oxidase, a glutamate oxidase, a pyranose oxidase, a choline oxidase, a cellobiose dehydrogenase, a glucose dehydrogenase, a pyranose dehydrogenase, a fructose dehydrogenase, an aldehyde oxidase, a gluconolactone oxidase, an alcohol dehydrogenase, an ascorbate oxidase, a sulfide dioxygenase, a laccase, and bilirubin oxidase.

8. The battery of claim 1, wherein the anode or cathode is selected from the group consisting of: graphite, a solid support with enzyme tethered, a biofilm, Pt, carbon, Ag, a noble metal, stainless steel, lead, gold, palladium, and combinations thereof.

9. The battery of claim 1, wherein a half cell reaction at the anode includes a bacterial catalyst.

10. The battery of claim 1, wherein the cathode comprises an intercalation material of transition metal oxides, polyanions or compounds that can reversibly intercalate alkali metal ion into their lattice.

11. The battery of claim 10, wherein the intercalation material is in an alkali ion-deinserted state.

12. The battery of claim 10, wherein the intercalation material is selected from the group consisting of: $Na_xMnO_2$, $MnO_2$, $NaCo_{1/3}Ni_{1/3}Mn_{1/3}PO_4$, $Na_2FeP_2O_7$, $NaVPO_4F$, $Na_3V_2(PO_4)_3$, $NaFePO_4$, $Na_3V_2O_{2x}(PO_4)_2F_{3-2x}$, $NaFe(SO_4)_2$, $NaCoO_2$, and cobalt oxide ($CoO_2$).

13. The battery of claim 1, wherein the cathode further comprises conversion reaction constituents selected from the group consisting of: oxides, fluorides, oxyfluorides, sulfides, nitrides, phosphides, $FeF_3$, and $CoF_2$.

14. The battery of claim 1, wherein the cathode further comprises metal-containing binary fluoride, metal-containing ternary fluoride, a complex fluoride, or an oxysalt.

15. The battery of claim 1, wherein the electrolyte on an anode side of the battery comprises a fuel selected from the group consisting of: a biologic waste, wastewater, compost, a food process waste, a sugar, an organic acid, and a biopolymer.

16. The battery of claim 1, further comprising a porous membrane between the anode and cathode.

17. The battery of claim 1, wherein there is no membrane in the electrolyte between the anode and cathode and the electrolyte is anaerobic.

18. The battery of claim 1, wherein the electrolyte is anaerobic and comprises an alkaline metal salt concentration ranging from 100 mM to 1.5 M.

19. The battery of claim 1, further comprising a mediators selected from the group consisting of: neutral red, $Mn^{4+}$, $Fe_3O_4$, $Ni^{2+}$, fluorinated polyanilines, anthraquinone-1,6-disolfonic acid (AQDS), and 1,4-naphthoquinone (NQ), coated on a surface of the anode or in the electrolyte.

20. The battery of claim 1, wherein the battery further comprises a container enclosing the electrolyte and the container comprises an inlet port and outlet port allowing the electrolyte to be refreshed.

21. The battery of claim 20, adapted to allow the electrolyte to be refreshed continuously or refreshed in a batch mode.

22. The battery of claim 1, wherein a half cell reaction at the anode comprises $CH_3COO^- + 4H_2O \rightarrow 2HCO_3^{2-} + 9H^+ + 8e^-$ or a half cell reaction at the cathode comprises $CoO_2 + xNa^+ + xe^- \rightarrow Na_xCoO_2$.

23. The battery of claim 1, the bioactive material is a microbe selected from the group consisting of: a bacterium, a fungus, an alga, an archaebacterium, a protist, a plankton, *geobacter*, halophile, and a *Halobacterium*.

24. A method of generating a DC current, the method comprising:
   providing the biologic battery of claim 1; and,
   providing an organic feed stock in the electrolyte, which feed stock is metabolized by the bioactive material or enzymatically converted by the bioactive material into the organic electron donor molecule;
   wherein the electron donor molecule donates an electron at the anode to be conducted through the conductor to the cathode.

25. The battery of claim 1, wherein oxygen is not present at the cathode in use.

* * * * *